United States Patent
Maul et al.

[11] Patent Number: 6,078,045
[45] Date of Patent: Jun. 20, 2000

[54] PROCESS FOR ANALYSIS OF A SAMPLE

[75] Inventors: Johann L. Maul, Indersdorf, Germany; M. G. Dowsett, Balsall Common, United Kingdom

[73] Assignee: Atomika Instruments GmbH, Oberschleibheim, Germany

[21] Appl. No.: 09/076,936

[22] Filed: May 13, 1998

[51] Int. Cl.[7] .............................. H01J 49/26; H01J 49/00; G01N 23/00
[52] U.S. Cl. .......................... 250/309; 250/281; 250/282
[58] Field of Search ..................................... 250/309, 281, 250/282

[56] References Cited

U.S. PATENT DOCUMENTS

| | | | |
|---|---|---|---|
| 5,164,594 | 11/1992 | Thompson et al. | 250/288 |
| 5,350,919 | 9/1994 | Hirano et al. | 250/282 |
| 5,714,757 | 2/1998 | Itabashi et al. | 250/309 |

FOREIGN PATENT DOCUMENTS

| | | |
|---|---|---|
| 4205752 | 8/1993 | Germany . |
| 63-282641 | 11/1988 | Japan . |
| 7-65783 | 3/1995 | Japan . |

*Primary Examiner*—Edward P. Westin
*Assistant Examiner*—Nikita Wells
*Attorney, Agent, or Firm*—Helfgott & Karas, P.C.

[57] ABSTRACT

In a secondary ion mass spectrometry (SIMS) method for analysis of a sample, in a first process step, the kinetic energy of the emitted primary ions emitted by a primary ion source (2) is set to a relatively low value, so that the surface of the sample (1) is enriched with primary ions, and erosion of the surface of the sample (1) essentially does not take place, and in a second process step, the kinetic energy of the primary ions emitted by one and the same primary ion source (2) is set to a relatively high value, so that the surface of the sample (1) can be eroded by the primary ion beam, where the formation of secondary ions in the second process step is promoted by the primary ions implanted during the first process step. Over and above this, targeted, locally differentiated enrichment of the sample surface ("chemical gating") can be carried out.

9 Claims, 1 Drawing Sheet

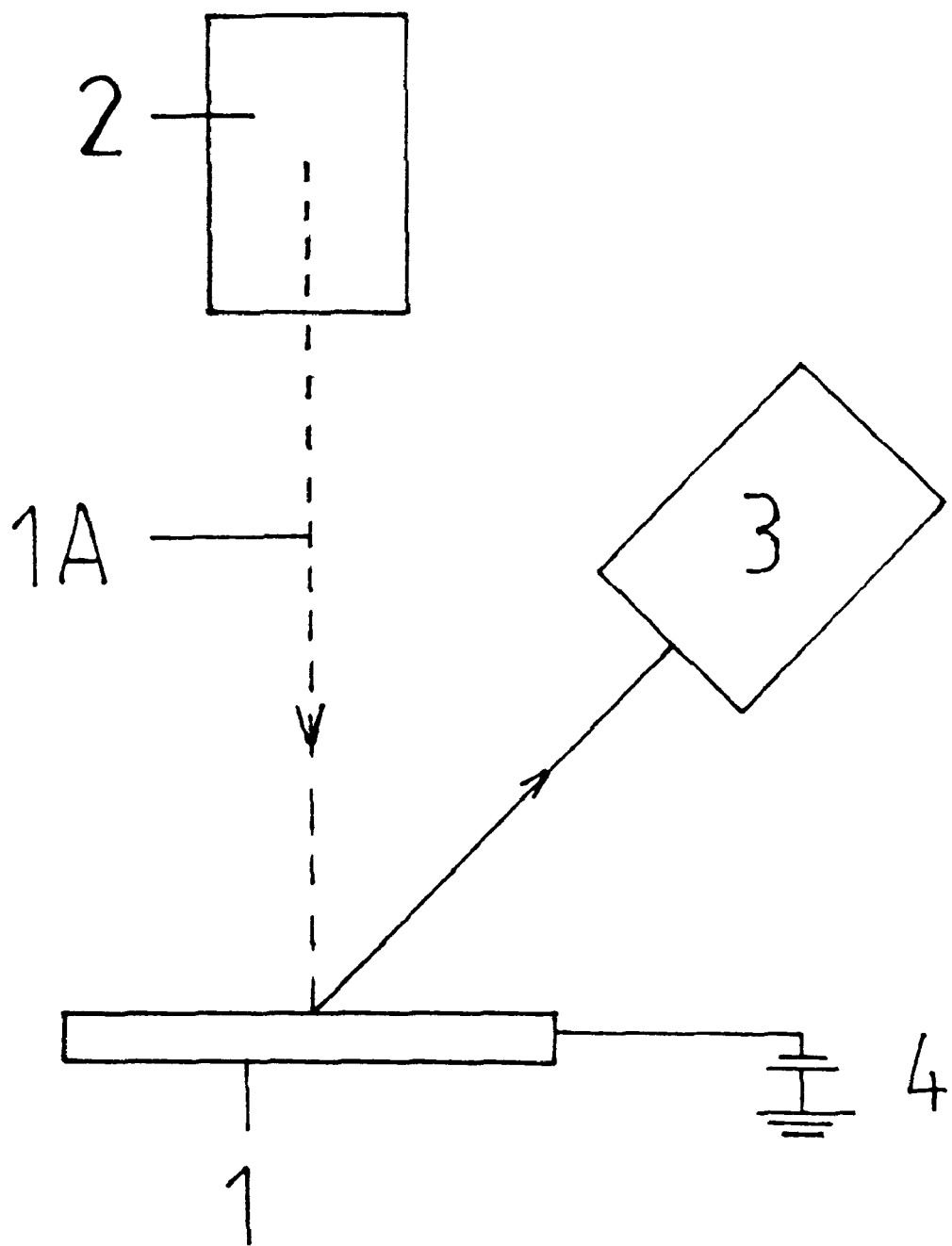
Fig.

PROCESS FOR ANALYSIS OF A SAMPLE

The invention relates to a process for analysis of a sample, pursuant to the preamble of claim 1, and to a device for implementing the process.

In the analysis of samples using secondary ion mass spectroscopy (SIMS), the intention is to achieve good depth resolution, low detection limits, and correction of false values caused by the so-called "tarnish effect", all at the same time. The "tarnish effect" is caused by the fact that as the sample starts to be eroded by the primary ions, the latter are partly implanted in the sample, and therefore promote further formation of secondary ions. A process is known according to which the primary ion beam which erodes the sample is aimed at the sample to be studied at an incidence angle of 45° degrees [sic] or more with reference to the normal relative to the sample surface. Such a process has the advantage that the concentration of a doping material in a solid sample, for example, can be measured with better depth resolution. The disadvantage of this process, however, is that in general, the yield of secondary ions which are emitted by the sample and therefore the detection sensitivity are reduced, since the implantation of primary ions into the sample is reduced at the aforementioned high bombardment angles. It is known that this implantation of primary ions into the sample, which is relatively strong at perpendicular bombardment, promotes the formation of secondary ions, particularly, if an electropositive or electronegative type of primary ion, respectively, is selected (preferably cesium or oxygen, respectively), the formation of negative or positive secondary ions, respectively.

In the German patent DE-PS 42 05 752, an arrangement is described with which this reduction in secondary ion yield can be compensated to a great extent. The arrangement provides that a second particle beam with relatively low kinetic energy is aimed at the sample at a perpendicular incidence, and thereby causes particles of this type, preferably oxygen or cesium, to accumulate in a region of the sample close to the surface. The second particle beam source can either be operated simultaneously with the first particle beam source, and thereby the sample can be enriched simultaneously as the primary ions erode it, or it can be operated in interval operation with the first particle beam source. While the arrangement described optimizes the three requirements stated initially, to a great extent, it has the disadvantage that it becomes relatively voluminous and inconvenient because two particle beam sources have to be set up.

The present invention therefore is based on the task of indicating an improved process for secondary ion mass spectroscopy and a device for implementing the process, by means of which the requirements stated initially can be optimized at the same time, and a relatively simple structure is made possible.

This task is accomplished by the characterizing characteristics of claim 1.

Accordingly, the process according to the invention provides that in a first process step, the kinetic energy of the primary ions emitted by the primary ion source is set to a relatively low value, so that the surface of the sample is enriched with primary ions, and erosion of the surface of the sample by sputtering essentially does not take place, and that in a second process step, the kinetic energy of the primary ions emitted by the primary ion source is set to a relatively high value, so that the surface is eroded by the primary ion beam.

Therefore one and the same particle beam source is used both for enriching the sample and for eroding it, which makes a device for implementing the process relatively compact.

Advantageous further developments are indicated in the dependent claims. In particular, according to these, the kinetic energy of the primary ions can be set either by setting the emission parameters of the primary ion source or by varying a potential which is applied to the sample. Independent claims 8 and 9 relate to devices for implementing the process.

The figure schematically shows a device for implementing the process.

For analysis of a sample 1, a primary ion beam of a primary ion source 2 is aimed at the sample surface at any desired bombardment angle with reference to the normal relative to the sample surface, and the secondary ions released by the sample are analyzed in a mass spectrometer 3. In the principle diagram of the figure, the bombardment angle is 0° degrees [sic]. The bombardment angle can, however, also be greater, for example, particularly if an improvement in depth resolution can be expected as a result. This is the case, for example when using cesium as the type of primary ion. The mass spectrometer 3 is preferably aligned at an angle of approximately 90° degrees [sic] with its ion-optical axis, with reference to the primary ion beam.

In the first process step, the energy of the particle beam 1A is preferably less than the threshold energy for sputtering sample 1, in other words typically less than 50 eV. Therefore a region of sample 1 which is close to the surface is enriched with primary ions, preferably oxygen or cesium ions. In the second process step, the energy of the primary ions is significantly increased, for example to a value of 150 eV to 10 keV, but preferably to a value greater than 1 keV, so that sample 1 can be eroded by the ion bombardment. As already explained, the primary ions implanted in the first process step promote the formation of the secondary ions in the second process step.

A significant advantage of the process lies in the fact that the "tarnish effect" described initially can be avoided, since a region close to the surface is enriched right from the start, in the first process step. Therefore a high yield of secondary ions is achieved in the sputtering of the second process step, right from the start, so that the same conditions for analysis are present over the entire depth range, including the surface.

In accordance with a first embodiment of the invention, the kinetic energy of the primary ions is adjusted by a suitable selection of the emission parameters of primary ion source 2. The kinetic energy of the primary ions at the exit of primary ion source 2 should be adjustable over as large a range as possible, from <50 eV to >5000 eV. It should be possible to change the energy without mechanical intervention, if at all possible, i.e. merely by changing electrical potentials at the electrodes or the like, preferably with computer control. Preferably, the focus diameter of the primary ion beam should be smaller in the second process step than in the first process step, in order to guarantee that in the analysis, only those regions of the sample are eroded which were implanted in the first process step. In advantageous manner, production of a smaller focus in the second process step generally results from the higher ion energy, or is at least facilitated ion-optically by the latter. Furthermore, the precise selection of the energy of the primary ions in the second process step also depends on the requirements with regard to lateral resolution and depth resolution in the analysis. If good depth resolution is the goal, at the expense of lateral resolution, the ion energy is set to a relatively low value. Vice versa, a relatively high value for the ion energy is selected for good lateral resolution at the expense of depth resolution. The value for the ion energy can also be varied with location selectivity, for example if high depth resolution is desired for certain regions of the sample, while lesser depth resolution appears sufficient for other regions of the sample. Furthermore, different ion energies can also be selected during the analysis, following each other in time, for example if different depth resolutions are desired in different depth regions.

In accordance with a second embodiment of the invention, the kinetic energy of the primary ions is adjusted in that sample 1 is connected with a direct current source 4 and thereby has a potential applied to it, by which the primary ions are influenced. This has the advantage that the ion source does not have to be changed, and therefore can be structured in relatively simple manner. For example, the primary ion energy can be set to a constant 250 eV in both process steps, while the sample is at a positive potential of 200 V during the first process step, so that the primary ions are braked to an energy of 50 eV. In the second process step of sputtering, the sample potential is then reduced to 0 V, for example, so that the primary ions reach the sample with their initial energy of 250 eV.

The two process steps of implantation and erosion can also be carried out alternately, several times, with an implantation step always being inserted after a certain layer thickness has been eroded. This can prove to be advantageous particularly in the analysis of depth profiles with a greater depth.

The accumulation of oxygen or cesium can also be carried out in such a way that only selected locations of the sample are enriched with oxygen or cesium and therefore the degree of ionization is increased only at these locations. This has the result that regions of the sample which disrupt the measurement are less pronounced, since they were not enriched with oxygen or cesium. In the case of depth profile measurements, this "chemical gating" can be carried out by alternating between high (>200 eV) and low primary ion energies (<100 eV) during the entire depth profile measurement.

We claim:

1. Process for analysis of a sample (1), with a primary ion source (2) and a mass spectrometer (3), where a primary ion beam (1A) emitted by the primary ion source (2) is aimed at the surface of the sample (1) during the analysis, and the mass spectrometer (3) detects the secondary ions emitted by the sample (1), characterized in that in a first process step, the kinetic energy of the emitted primary ions is set to a relatively low value, so that the surface of the sample (1) is enriched with primary ions, and erosion of the surface of the sample (1) essentially does not take place, and that in a second process step, the kinetic energy of the primary ions is set to a relatively high value, so that the surface of the sample (1) is eroded by the primary ion beam.

2. Process according to claim 1, characterized in that the kinetic energy of the primary ions is adjusted by changing the parameters of the primary ion source (2).

3. Process according to claim 1, characterized in that the sample (1) has an electrical potential applied to it and that the kinetic energy of the primary ions is adjusted by changing the potential.

4. Process according to claim 2 or 3, characterized in that the kinetic energy of the primary ions in the first process step is less than 50 eV.

5. Process according to claim 1, characterized in that the kinetic energy of the primary ions in the second process step is greater than 150 eV.

6. Process according to claim 1, characterized in that the first and the second process step are carried out several times, alternately.

7. Process according to claim 1, characterized in that selected locations on the sample are enriched with primary ions in the first process step, so that non-selected sample regions are less evident in the measurement during the second step.

8. Device for implementing the process according to claim 2, with a primary ion source (2) which is aligned, with regard to the sample (1) to be investigated, in such a way that a primary ion beam (1A) emitted by the primary ion source (2) impacts on the sample (1), and a mass spectrometer (3) for detection of the secondary ions emitted by the sample (1), characterized in that the kinetic energy of the primary ions can be adjusted by means of the primary ion source (2).

9. Device for implementing the process according to claim 3, with a primary ion source (2) which is aligned, with regard to the sample (1) to be investigated, in such a way that a primary ion beam (1A) emitted by the primary ion source (2) impacts on the sample (1), and a mass spectrometer (3) for detection of the secondary ions emitted by the sample (1), characterized in that the sample (1) is connected with a direct voltage source (4) and the kinetic energy of the primary ions can be adjusted by means of adjusting the electrical potential of the sample (1).

* * * * *